United States Patent
Kim et al.

(10) Patent No.: US 10,201,437 B2
(45) Date of Patent: Feb. 12, 2019

(54) WEARABLE ROBOT AND CONTROL METHOD THEREOF

(71) Applicant: Samsung Electronics Co., Ltd., Suwon-Si, Gyeonggi-Do (KR)

(72) Inventors: Ji Young Kim, Anyang-si (KR); Kyung-Won Moon, Yongin-si (KR); Young Bo Shim, Seoul (KR); Ju Suk Lee, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/558,081

(22) Filed: Dec. 2, 2014

(65) Prior Publication Data
US 2015/0196403 A1 Jul. 16, 2015

(30) Foreign Application Priority Data

Jan. 15, 2014 (KR) .......................... 10-2014-0005139

(51) Int. Cl.
*A61F 2/68* (2006.01)
*A61F 2/70* (2006.01)
(Continued)

(52) U.S. Cl.
CPC .............. *A61F 2/70* (2013.01); *A61H 1/024* (2013.01); *A61H 1/0244* (2013.01); *A61H 1/0266* (2013.01); *A61H 3/00* (2013.01); *A61F 2/68* (2013.01); *A61F 2/72* (2013.01); *A61F 2002/6818* (2013.01);
(Continued)

(58) Field of Classification Search
CPC ........................................................ A61F 2/70
See application file for complete search history.

(56) References Cited

U.S. PATENT DOCUMENTS 6,500,138 B1 * 12/2002 Irby ..................... A61F 5/0125
602/26
2003/0120183 A1 * 6/2003 Simmons .................. A61F 4/00
600/595

(Continued)

FOREIGN PATENT DOCUMENTS

JP          2001277159 A      10/2001
KR     1020110083144 A       7/2011

OTHER PUBLICATIONS

Duschau-Wicke, A., et al, "Path Control: A Method for Patient-Cooperative Robot-Aided Gait Rehabilitation," Neural Systems and Rehabilitation Engineering, IEEE Transactions on pp. 38-48, Feb. 2010.

(Continued)

*Primary Examiner* — Jacqueline Woznicki
(74) *Attorney, Agent, or Firm* — Harness, Dickey & Pierce, P.L.C.

(57) ABSTRACT

Disclosed herein is a control method of a wearable robot, including: generating reference gait data based on the results of sensing by a sensor unit included in a structure; estimating, when a wearer walks, the wearer's gait phase based on the results of sensing by the sensor unit; detecting a gait phase having a minimum difference from the estimated gait phase from the reference gait data; and driving a driver of the structure, according to a control signal generated based on the estimated gait phase and the detected gait phase.

7 Claims, 8 Drawing Sheets

(51) Int. Cl.
  *A61F 2/72* (2006.01)
  *A61H 3/00* (2006.01)
  *A61H 1/02* (2006.01)
(52) U.S. Cl.
  CPC .............. *A61F 2002/6827* (2013.01); *A61F 2002/6836* (2013.01); *A61F 2002/6845* (2013.01); *A61F 2002/6863* (2013.01); *A61F 2002/701* (2013.01); *A61F 2002/702* (2013.01); *A61F 2002/704* (2013.01); *A61F 2002/705* (2013.01); *A61F 2002/707* (2013.01); *A61F 2002/708* (2013.01); *A61H 2201/0192* (2013.01); *A61H 2201/1215* (2013.01); *A61H 2201/1238* (2013.01); *A61H 2201/164* (2013.01); *A61H 2201/165* (2013.01); *A61H 2201/1623* (2013.01); *A61H 2201/1628* (2013.01); *A61H 2201/5007* (2013.01); *A61H 2201/5061* (2013.01); *A61H 2201/5064* (2013.01); *A61H 2201/5069* (2013.01); *A61H 2201/5079* (2013.01); *A61H 2201/5084* (2013.01); *Y10S 901/09* (2013.01); *Y10S 901/23* (2013.01); *Y10S 901/46* (2013.01)

(56) References Cited

U.S. PATENT DOCUMENTS

| | | |
|---|---|---|
| 2006/0135883 A1* | 6/2006 | Jonsson ............... A61F 2/6607 600/546 |
| 2007/0016116 A1 | 1/2007 | Reinkensmeyer et al. |
| 2007/0016329 A1* | 1/2007 | Herr .................... B62D 57/032 700/250 |
| 2008/0255488 A1* | 10/2008 | Agrawal .......... A63B 21/00181 602/23 |
| 2009/0030344 A1* | 1/2009 | Moser ................... A61B 5/112 600/587 |
| 2010/0271051 A1 | 10/2010 | Sankai et al. |
| 2015/0039098 A1* | 2/2015 | van der Merwe ..... G05B 15/02 623/25 |

OTHER PUBLICATIONS

Aoyagi, D. et al. "A Robot and Control Algorithm That Can Synchronously Assist in Naturalistic Motion During Body-Weight-Supported Gait Training Following Neurologic Injury," Neural Systems and Rehabilitation Engineering, IEEE Transactions on , pp. 3887-400. Sep. 2007.

* cited by examiner

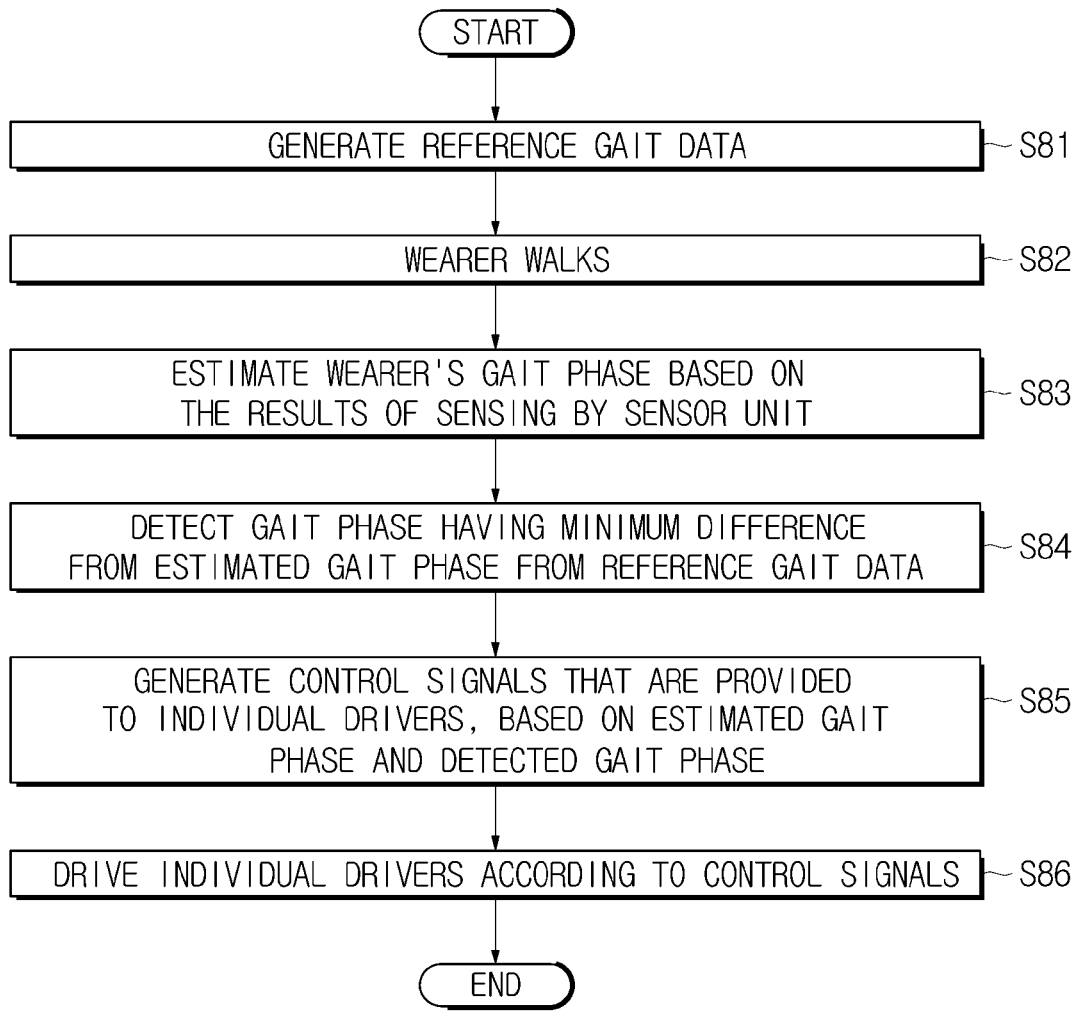

WEARABLE ROBOT AND CONTROL METHOD THEREOF

CROSS-REFERENCE TO RELATED APPLICATION

This application claims the benefit of Korean Patent Application No. 2014-0005139, filed on Jan. 15, 2014 in the Korean Intellectual Property Office, the entire disclosure of which is incorporated herein by reference.

BACKGROUND

1. Field

Example embodiments relate to a wearable robot and a control method thereof, wherein a motion of the wearable robot can be synchronized with a wearer's motion when the wearable robot is controlled based on reference gait data.

2. Description of the Related Art

Robots are used for various purposes in military, industrial, and medical fields. Wearable robots have been developed to help and assist peoples having difficulty in walking in interior and exterior environments. The wearable robots can be classified into support-type wearable robots (hereinafter, simply referred to as support-type robots), and wearing-type wearable robots (hereinafter, simply referred to as wearable robots).

The support-type robot may determine a user's walking intention to assist his/her walking. The support-type robot may include a body, a handle bar mounted on the body, and a plurality of wheels provided in the lower part of the body to move the body.

The wearable robot is used to help rehabilitation and muscle power enhancement of elderly peoples and patients having low physical strength of lower extremity. The wearable robot has an exoskeleton structure such that it can be worn on a user's lower extremity.

SUMMARY

Therefore, example embodiments provide a wearable robot and a control method thereof. In some example embodiments, a wearable robot is configured to synchronize a motion of the wearable robot with a wearer's motion by controlling the wearable robot based on reference gait data.

Additional aspects of the example embodiments will be set forth in part in the description which follows and, in part, will be obvious from the description, or may be learned by practice of the example embodiments.

Some example embodiments relate to a control method of a wearable robot.

In some example embodiments, the control method includes: generating reference gait data based on the results of sensing by a sensor unit included in a structure; estimating, when a wearer walks, the wearer's gait phase based on the results of sensing by the sensor unit; detecting a gait phase having a minimum difference from the estimated gait phase from the reference gait data; and driving a driver of the structure, according to a control signal generated based on the estimated gait phase and the detected gait phase.

In other example embodiments, the control method of a wearable robot, including: estimating, when a wearer walks, the wearer's gait phase based on the results of sensing by a sensor unit included in a structure; detecting a gait phase having a minimum difference from the estimated gait phase from reference gait data acquired in advance; and driving a driver of the structure, according to a control signal generated based on the estimated gait phase and the detected gait phased.

In other example embodiments, the wearable robot including: a storage unit configured to store reference gait data; a structure having an exoskeleton shape such that the structure is able to be worn on a wearer's leg, the structure including a sensor unit; and a controller configured to estimate, when the wearer walks, the wearer's gait phase based on the results of sensing by the sensor unit, to detect a gait phase having a minimum difference from the estimated gait phase from the reference gait data, and to drive a driver of the structure, according to a control signal generated based on the estimated gait phase and the detected gait phase.

BRIEF DESCRIPTION OF THE DRAWINGS

These and/or other aspects of the example embodiments will become apparent and more readily appreciated from the following description of the embodiments, taken in conjunction with the accompanying drawings of which:

FIG. 8 is a flowchart illustrating a control method of a wearable robot according to some example embodiments.

DETAILED DESCRIPTION

Figure 1:
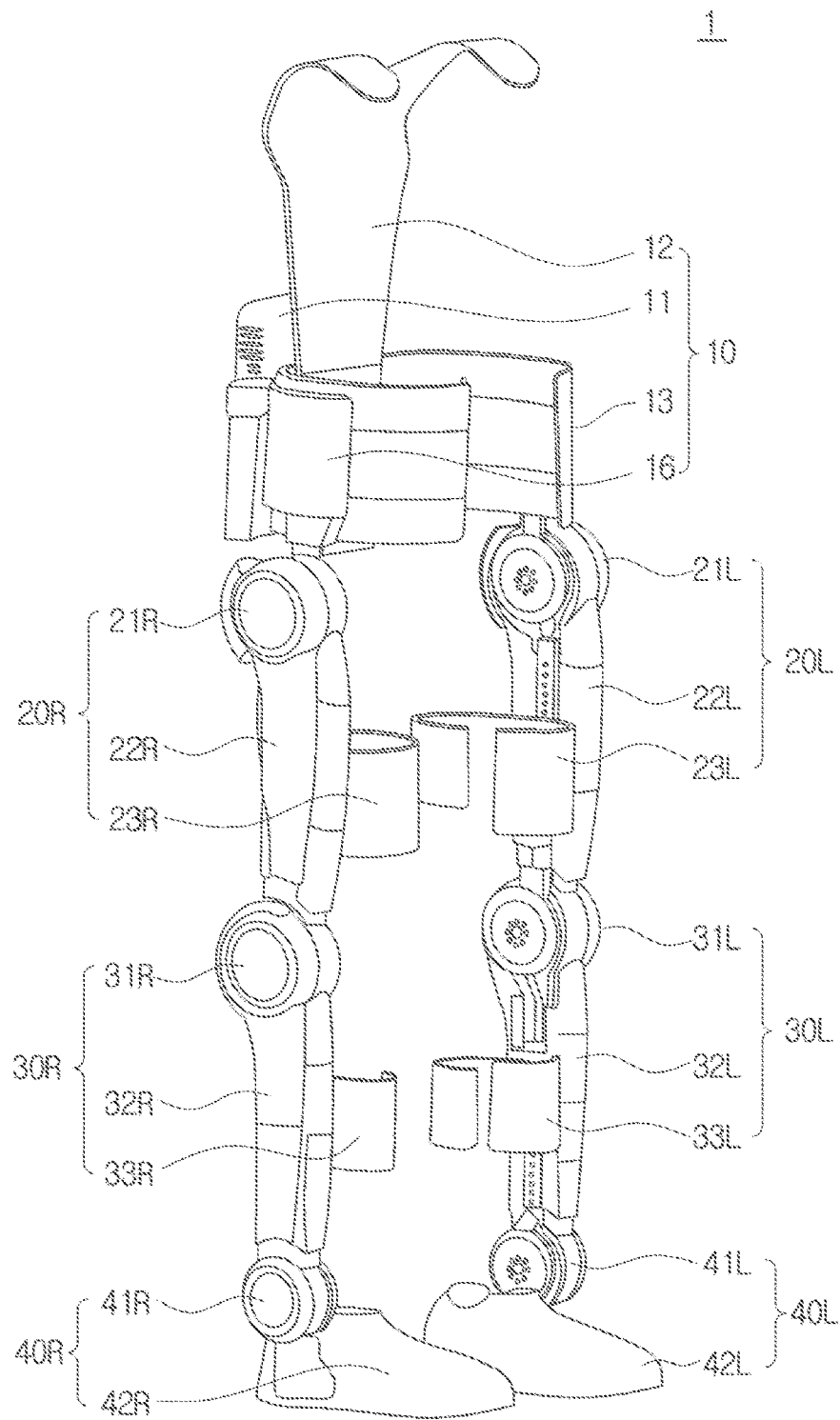
FIG. 1 is a perspective view illustrating a front part of a wearable robot according to some example embodiments.

Reference will now be made in detail to example embodiments, some examples of which are illustrated in the accompanying drawings, wherein like reference numerals refer to like elements throughout.

Hereinafter, a wearable robot and a control method thereof according to some example embodiments will be described with reference to the appended drawings.

In the drawings, the thicknesses of layers and regions are exaggerated for clarity. Like reference numerals in the drawings denote like elements.

Detailed illustrative embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

In the following description, a robot may include a mobile robot and a wearable robot. The mobile robot may include an unmanned robot that can move without setting a person thereon, and a manned robot on which a person can ride. The wearable robot may include a support-type robot and a wearing-type robot.

The support-type robot may include a body that can be moved by a plurality of wheels, and a handle bar which is mounted on the upper part of the body, with which a user can adjust a moving direction of the body, and against which the user can lean.

The wearing-type robot may have an exoskeleton structure so that it can be worn on at least one leg of a wearer's both legs. In the following description, the wearing-type robot will be described as an example of a wearable robot.

Figure 2:
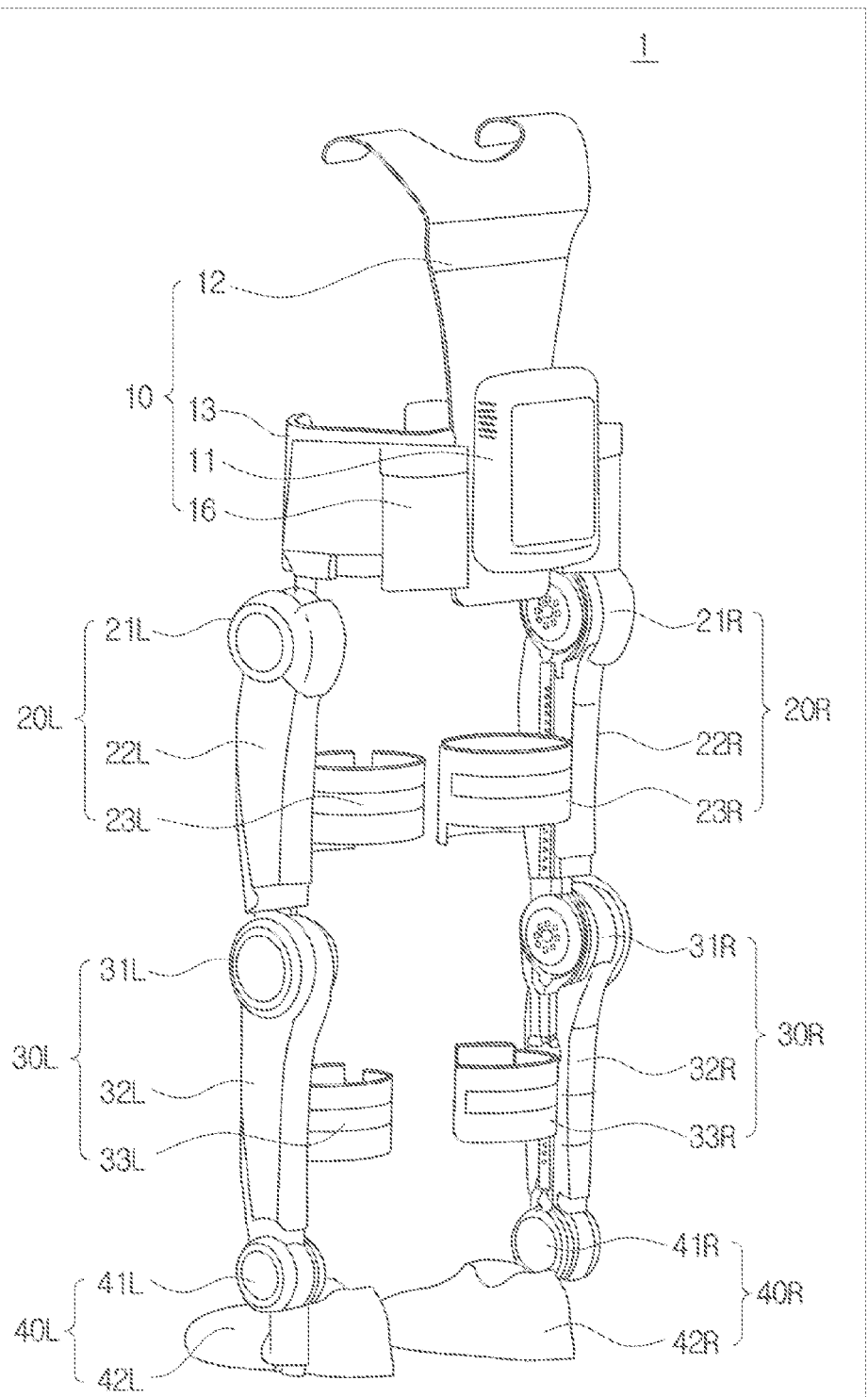
FIG. 2 is a perspective view illustrating a rear part of a wearable robot according to some example embodiments.

FIGS. 1 and 2 illustrate a wearable robot according to some example embodiments. FIG. 1 is a perspective view illustrating a front part of a wearable robot according to some example embodiments, and FIG. 2 is a perspective view illustrating a rear part of a wearable robot according to an embodiment of the present disclosure.

As shown in FIGS. 1 and 2, a wearable robot 1 has an exoskeleton structure such that it can be worn on a wearer's left and right legs. The wearer wearing the wearable robot 1 can perform motions, such as extension, flexion, adduction, abduction, etc. The extension is a motion of extending joints, and the flexion is a motion of bending joints. The adduction is a motion of gathering legs toward the central axis of the body, and the abduction is a motion of spreading legs away from the central axis of the body.

Referring to FIGS. 1 and 2, the wearable robot 1 may include a main body 10, first structures 20R and 20L, second structures 30R and 30L, and third structures 40R and 40L.

The main body 10 may include a housing 11, a waist securing unit 13, a waist supporting unit 12, and a power supply 16.

The housing 11 may accommodate various components therein. The components may include a Central Processing Unit (CPU), a Graphic Processing Unit (GPU), a Printed Circuit Board (PCB), various kinds of storage units, and an Inertial Measurement Unit (IMU).

The PCB is a board on which predetermined circuitry is printed, and the CPU, the GPU, the various kinds of storage units, and the IMU may be mounted on the PCB. The PCB may be fixedly mounted on the inner side surface of the housing 11.

The CPU may be a micro processor. The micro processor is a processing device in which an Arithmetic Logic Unit (ALU), a register, a program counter, a command decoder, a control circuit, etc. are installed in a silicon chip. The CPU may generate control signals for controlling operations of the first to third structures 20R, 20L, 30R, 30L, 40R, and 40L. For example, the CPU may generate control signals for driving the first to third structures 20R, 20L, 30R, 30L, 40R, and 40L, according to reference gait data of the wearable robot 1. The reference gait data may be generated in advance. Also, the CPU may estimate the wearer's gait phase based on information sensed by various sensors of a sensor unit to generate an estimated gait phase, and detect a gait phase among the reference gait data whose difference is relatively close to the estimated gait phase. In some example embodiments, the detected gait phase may have a minimum difference from the estimated gait phase. The detected gait phase may be a phase of a movement cycle of limbs of wearer of the wearable robot 1 during locomotion over the ground. For example, a phase within the gait cycle of FIG. 4. Then, the CPU may adjust driving velocities of individual drivers such that the estimated gait phase gradually converges into the detected gait phase.

The GPU is a processing device for processing information related to graphics in the micro processor. The GPU may assist a graphic processing function of the CPU, or may perform graphic processing independently.

The IMU may include an inertial sensor. The inertial sensor may measure an acceleration and an angular velocity. The IMU may be mounted on the PCB.

The housing 11 may accommodate various kinds of storage units therein. The storage units may include a magnetic disk storage device that magnetizes the surface of a magnetic disk to store data, and a semiconductor memory device that stores data using various kinds of memory semiconductors.

The IMU included in the housing 11 may include an inertial sensor. The inertial sensor may measure an acceleration and an angular velocity of the wearable robot 1.

The power supply 16 may be provided outside the housing 11. The power supply 16 may supply power to various components installed in the housing 11 or to the first to third structures 20R, 20L, 30R, 30L, 40R, and 40L. FIGS. 1 and 2 show a case where the power supply 16 is disposed outside the housing 11, however, the power supply 16 may be disposed inside the housing 11. Specifically, the power supply 16 may be mounted on the PCB installed in the housing 11. The power supply 16 may be separated from the housing 11 or from the PCB in the housing 11, or the power supply 16 may be charged by an external device (not shown).

The waist securing unit 13 functions to dispose the housing 11 on the wearer's waist. The waist securing unit 13 may have a shape of a curved plate so as to support the wearer's waist. Although not shown in the drawings, the waist securing unit 13 may further include a fastening unit for fastening the waist securing unit 13 on the wearer's waist. The fastening unit may be implemented with a band or a belt. The length of the fastening unit may be adjustable. In this case, the fastening unit may fasten the waist securing unit 13 on the wearer's waist regardless of the wearer' waist circumference.

The waist supporting unit 12 may be connected to the waist securing unit 13. The waist supporting unit 12 may have a shape of a curved plate so as to support the wearer's back, and have a curved shape whose one end can be put on the wearer's both shoulders, as shown in FIGS. 1 and 2. However, the shape of the waist supporting unit 12 is not limited to this, and the waist supporting unit 12 may have a specific shape corresponding to the shape of the wearer's back and/or shoulders.

The first structures 20R and 20L may support movements of the wearer's hip joints and thighs when the wearer walks. To do this, the first structures 20R and 20L may include first joints 21R and 21L, first links 22R and 22L, and first securing units 23R and 23L.

The first joints 21R and 21L may correspond to a human body's hip joints. The first joints 21R and 21L may rotate within the operating range of the wearer's hip joints. To do this, the first joints 21R and 21L may have at least 1 Degree of Freedom (DOF).

Herein, the DOF is a DOF in Forward Kinematics or in Inverse Kinematics. DOF of mechanism means the number of independent motions of mechanism, or the number of independent parameters that are required to specify an independent motion at a relative position with respect to links. For example, an object that is in a 3Dimensional (3D) space composed of x-, y-, and z-axes has one or more DOF of 3 DOF (positions on the respective axes) to specify a spatial position of the object, and 3 DOF (rotation angles with respect to the respective axes) to specify a spatial orientation of the object. If a certain object is movable on the individual axes and rotatable with respect to the individual axes, the object can be understood to have 6 DOF.

As discussed below with reference to FIG. 5, first drivers 210R and 210L may be provided in the first joints 21R and 21L. The first drivers 210R and 210L may be driven according to control signals that are provided from the main body 10, and generate various magnitudes of rotatory power in predetermined directions. The rotatory power generated by the first drivers 210R and 210L may be applied to the first links 22R and 22L connected to the first joints 21R and 21L.

The first drivers 210R and 210L may be ones of motors, vacuum pumps, and hydraulic pumps. However, the first drivers 210R and 210L are not limited to these. In the following description, the first drivers 210R and 210L are assumed to be motors.

Position sensors and velocity sensors may be provided in the first joints 21R and 21L. When the wearer walks, the position sensors may sense positions of the first joints 21R and 21L, and the velocity sensors may sense velocities of the first joints 21R and 21L.

The first links 22R and 22L may be physically connected to the first joints 21R and 21L. The first links 22R and 22L may rotate in desired (or, alternatively, predetermined) directions according to rotatory power generated by the first drivers 210R and 210L of the first joints 21R and 21L.

The first links 22R and 22L may be designed in various shapes. For example, the first links 22R and 22L may be configured with a plurality of nodes connected to each other. In this case, joints may be disposed between nodes, and the first links 22R and 22L may be bent within a desired (or, alternatively, predetermined) range by the joints. As another example, the first links 22R and 22L may be designed in a bar shape. In this case, the first links 22R and 22L may be made of a flexible material so that the first links 22R and 22L can be bent within a desired (or, alternatively, a predetermined) range.

The first securing units 23R and 23L may be attached on the first links 22R and 22L, respectively. The first securing units 23R and 23L function to secure the first links 22R and 22L on the wearer's thighs. FIGS. 1 and 2 show a case in which the first links 22R and 22L are secured on the outer sides of the wearer's thighs by the first securing units 23R and 23L. If the first links 22R and 22L move according to rotations of the first joints 21R and 21L, the wearer's thighs on which the first links 22R and 22L are secured move accordingly in the movement directions of the first links 22R and 22L. According to some example embodiments, each of the first securing units 23R and 23L may be implemented with an elastic band, an elastic belt, an elastic strap, a flexible metal material, or a combination of two or more of the above-mentioned materials.

The second structures 30R and 30L may support movements of the wearer's knee joints and shanks when the wearer walks. To do this, the second structures 30R and 30L may include second joints 31R and 31L, second links 32R and 32L, and second securing units 33R and 33L.

The second joints 31R and 31L correspond to a human body's knee joints. The second joints 31R and 31L may rotate within the operating range of the wearer's knee joints. To do this, the second joints 31R and 31L may have at least 1 Degree of Freedom (DOF).

Second drivers 310R and 310L (see FIG. 5) may be provided in the second joints 31R and 31L. The second drivers 310R and 310L may be driven according to control signals that are provided from the main body 10, and generate various magnitudes of rotatory power in desired (or, alternatively, predetermined) directions. The rotatory power generated by the second drivers 310R and 310L may be applied to the second links 32R and 32L connected to the second joints 31R and 31L.

The second drivers 310R and 310L may be ones of motors, vacuum pumps, and hydraulic pumps. However, the second drivers 310R and 310L are not limited to these. In the following description, the second drivers 310R and 310L are assumed to be motors.

Position sensors and velocity sensors may be provided in the second joints 31R and 31L. When the wearer walks, the position sensors may sense positions of the second joints 31R and 31L, and the velocity sensors may sense velocities of the second joints 31R and 31L.

The second links 32R and 32L may be physically connected to the second joints 31L and 31R. The second links 32R and 32L may rotate by a desired (or, alternatively, predetermined) angle according to rotatory power generated by the second drivers 310R and 310L of the second joints 31R and 31L.

The second links 32R and 32L may be designed in various shapes. For example, the second links 32R and 32L may be configured with a plurality of nodes connected to each other. In this case, joints may be disposed between nodes, and the second links 32R and 32L may be bent within a desired (or, alternatively, a predetermined) range by the joints. As another example, the second links 32R and 32L may be designed in a bar shape. In this case, the second links 32R and 32L may be made of a flexible material so that the second links 32R and 32L can be bent within a desired (or, alternatively, a predetermined) range.

The second securing units 33R and 33L may be attached on the second links 32R and 32L, respectively. The second securing units 33R and 33L function to secure the second links 32R and 32L on the wearer's shanks. FIGS. 1 and 2 show a case in which the second links 32R and 32L are secured on the outer sides of the wearer's shanks by the second securing units 33R and 33L. If the second links 32R and 32L move according to rotations of the second joints 31R and 31L, the wearer's shanks on which the second links 32R and 32L are secured move accordingly in the movement directions of the second links 32R and 32L. According to some example embodiments, each of the second securing units 33R and 33L may be implemented with an elastic band, an elastic belt, an elastic strap, a flexible metal material, or a combination of two or more of the above-mentioned materials.

The third structures 40R and 40L may support movements of the wearer's ankle joints and feet when the wearer walks. To do this, the third structures 40R and 40L may include third joints 41R and 41L and foot rest units 42R and 42L.

The third joints 41R and 41L correspond to a human body's ankle joints. The third joints 41R and 41L may rotate within the operating range of the wearer's ankle joints. To do this, the third joints 41R and 41L may have at least 1 DOF.

Third drivers 410R and 410L (see FIG. 5) may be provided in the third joints 41R and 41L. The third drivers 410R and 410L may be driven according to control signals that are provided from the main body 10, and generate various magnitudes of rotatory power in desired (or, alternatively, predetermined) directions. The rotatory power generated by the third drivers 410R and 410L may be applied to the foot rest units 43R and 43L connected to the third joints 41R and 41L.

The third drivers 410R and 410L may be ones of motors, vacuum pumps, and hydraulic pumps. However, the third drivers 410R and 410L are not limited to these. In the following description, the third drivers 410R and 410L are assumed to be motors.

Position sensors and velocity sensors may be provided in the third joints 41R and 41L. When the wearer walks, the position sensors may sense positions of the third joints 41R and 41L, and the velocity sensors may sense velocities of the third joints 41R and 41L.

Figure 3:
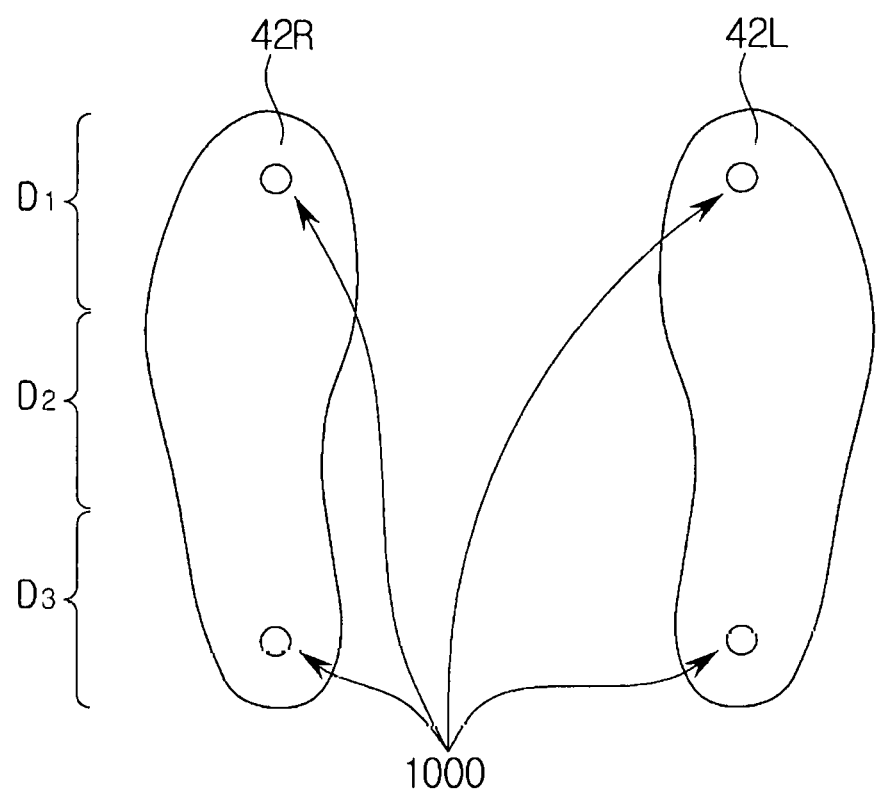
FIG. 3 is a bottom view of foot rest units of a wearable robot according to some example embodiments.

FIG. 3 is a bottom view of foot rest units of a wearable robot according to some example embodiments.

As illustrated in FIG. 3, pressure sensors may be disposed in the first area D1 and the third area D3 of each of the foot rest units 42R and 42L.

The foot rest units 42R and 42L may be provided to correspond to the locations of the wearer's feet, and physically connected to the third joints 41R and 41L. Each of the foot rest units 42R and 42L may include a pressure sensor, a force sensor, a load sensor, or a combination of two or more of the above-mentioned sensors. In the following description, a case in which each of the foot rest units 42R and 42L includes a pressure sensor will be described as an example.

For example, each of the foot rest units 42R and 42L may include two pressure sensors. The pressure sensors may be installed at different locations in the lower part of each of the foot rest units 42R and 42L. More specifically, each of the foot rest units 42R and 42L may include a first area D1 on which a forefoot (toes) is rested, a second area D2 on which a middle foot is rested, and a third area D3 on which a rearfoot (heel) is rested. The pressure sensors may be disposed in the first area D1 and the third area D3, respectively.

The pressure sensors disposed in the first area D1 and the third area D3 of each of the foot rest units 42R and 42L may be activated when the first area D1 and/or the third area D3 contacts the ground, and deactivated when the first area D1 and/or the third area D3 are taken off the ground. Operations of the pressure sensors according to a wearer's gait state will be described in more detail, below.

Figure 4:
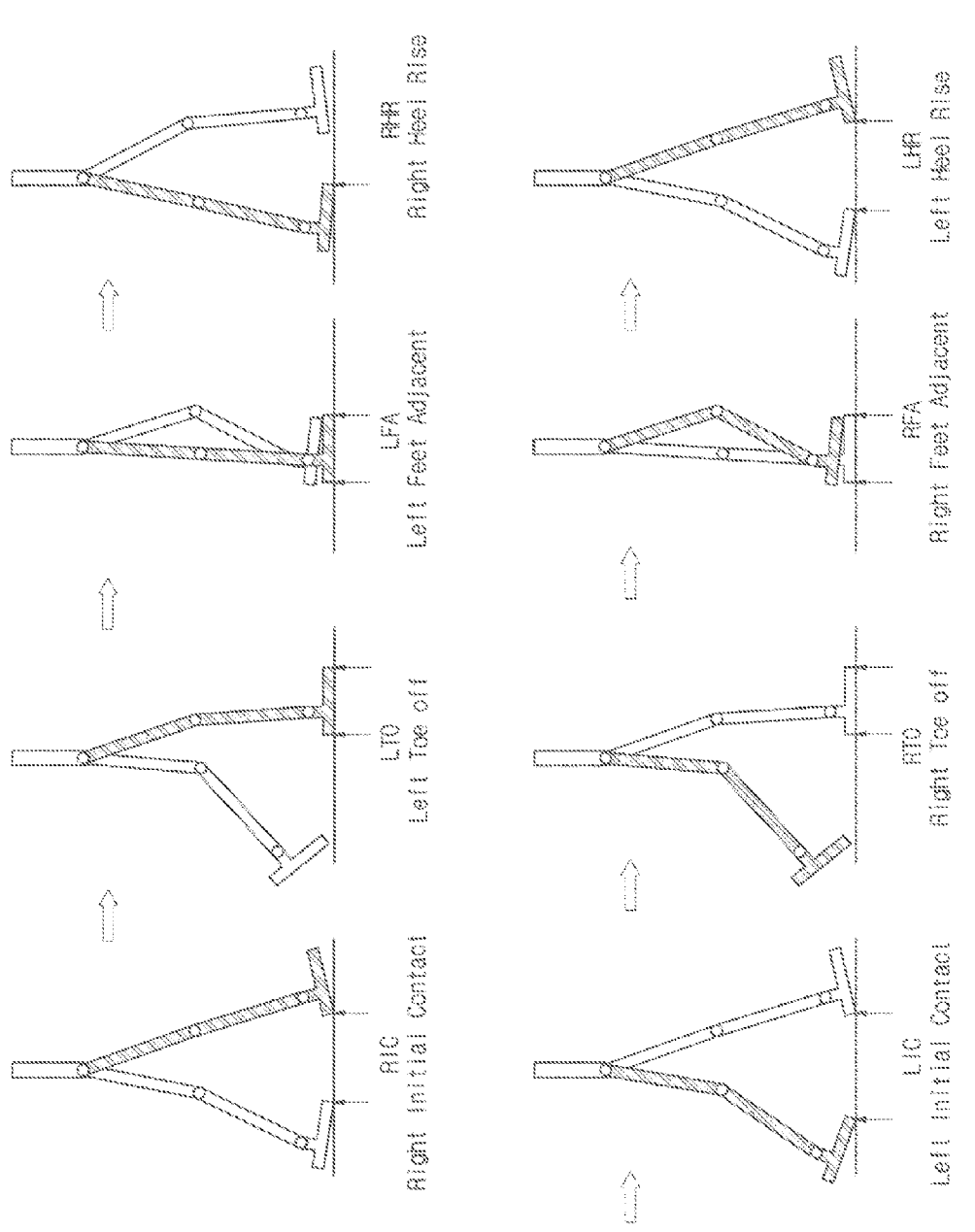
FIG. 4 shows a human's gait for a single gait cycle.

FIG. 4 shows a human's gait for a single gait cycle of a right leg. In FIG. 4, the right leg is shaded. A single gait cycle of a right leg is a time period from a time at which the heel of the right leg contacts the ground to a time at which the heel of the right leg again contacts the ground.

As illustrated in FIG. 4, in the gait cycle, the human's gait may be subdivided into 8 gestures: Right Initial contact (RIC), Left Toe Off (LTO), Left Feet Adjacent (LFA), Right Heel Rise (RHR), Left Initial Contact (LIC), Right Toe Off (RTO), Right Feet Adjacent (RFA), and Left Heel Rise (LFR).

In the Right Initial contact (RIC), since the right heel and the left toes contact the ground, the pressure sensor installed around the right heel and the pressure sensor installed around the left toes are activated.

In the Left Toe Off (LTO), since the right heel and the right toes contact the ground, the pressure sensor installed around the right heel and the pressure sensor installed around the right toes are activated. At this time, since the left foot is taken off the ground, all the pressure sensors installed around the left heel and the left toes are deactivated.

In the Left Feet Adjacent (LFA), like the LTO, the pressure sensor installed around the right heel and the pressure sensor installed around the right toes are activated. Since the left foot is still taken off the ground, all the pressure sensors installed around the left heel and the left toes are deactivated.

In the Right Heel Rise (RHR), since the right heel is taken off the ground and the right toes contact the ground, the pressure sensor installed around the right heel is deactivated, and the pressure sensor installed around the right toes is activated. Since the left foot is still taken off the ground, all the pressure sensors installed around the left heel and the left toes are deactivated.

In the Left Initial Contact (LIC), since the left heel and the right toes contact the ground, the pressure sensor installed around the left heel and the pressure sensor installed around the right toes are activated. Also, the pressure sensors installed around the left toes and the right heel are deactivated.

In the Right Toe Off (RTO), since the right foot is taken off the ground, and the left foot contacts the ground, all the pressure sensors installed around the right heel and the right toes are deactivated. Also, the pressure sensors installed around the left heel and the left toes are activated.

In the Right Feet Adjacent (RFA), like the RTO, all the pressure sensors installed around the right heel and the right toes are deactivated, and all the pressure sensors installed around the left heel and the left toes are activated.

In the Left Heel Rise (LFR), since the left heel and the right toes are taken off the ground, and the left toes and the right heel contact the ground, the pressure sensors installed around the left heel and the right toes are deactivated, and the pressure sensors installed around the left toes and the right heel are activated.

Figure 5:
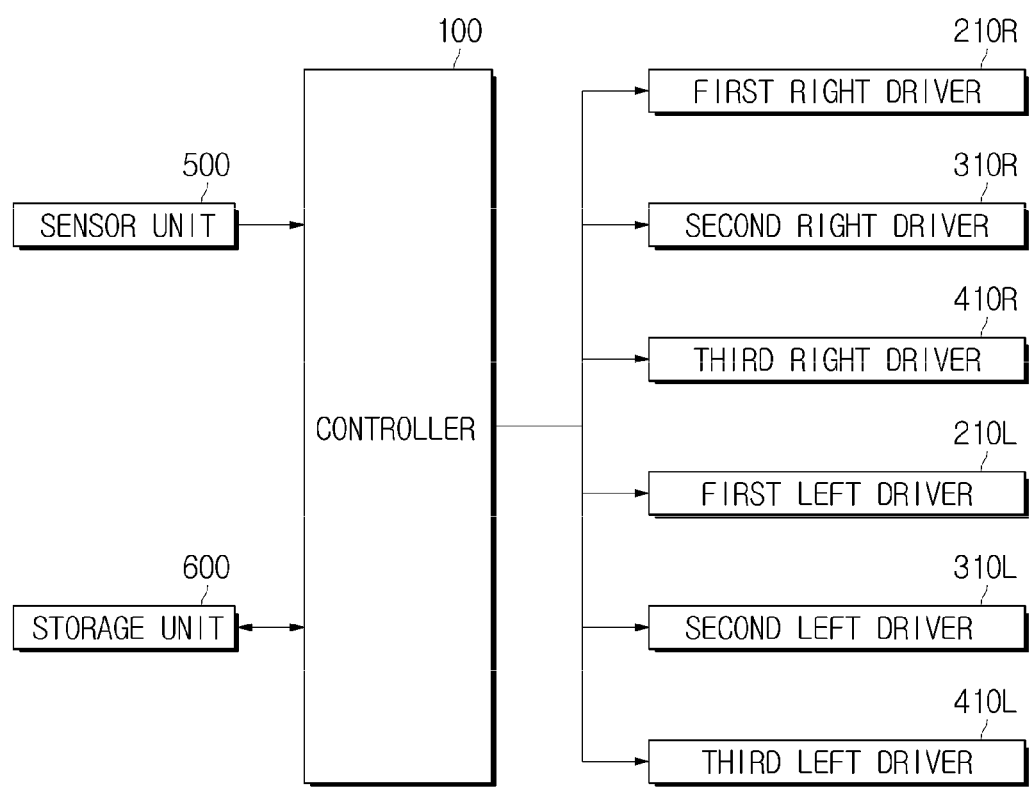
FIG. 5 is a block diagram illustrating a configuration of a wearable robot according to some example embodiments.

FIG. 5 is a block diagram illustrating a configuration of a wearable robot according to some example embodiments.

Referring to FIG. 5, a wearable robot 1 may include a controller 100, a sensor unit 500, a storage unit 600, and the plurality of drivers 210R, 210L, 310R, 310L, 410R, and 410L.

The sensor unit 500 may include various kinds of sensors. For example, the sensors may include at least one(s) of inertial sensors, position sensors, velocity sensors, and pressure sensors.

The position sensors and the velocity sensors may be disposed in the first joints 21R and 21L, the second joints 31R and 31L, and the third joints 41R and 41L (see FIG. 1), respectively. The position sensors and the velocity sensors disposed in the individual joints may sense positions and velocities of the corresponding joints when a wearer walks.

The pressure sensors may be disposed in the first area D1 and the third area D3 of each of the foot rest units 42R and 42L, as described above with reference to FIG. 3. The results of sensing by the pressure sensors may be used to determine whether the first area D1 and/or the third area D3 of each of the foot rest units 42R and 42L have contacted the ground. Also, the results of sensing by the pressure sensors may be used to estimate the wearer's current gait phase.

The storage unit 600 may store various data or algorithms needed for operations of the wearable robot 1. For example, the storage unit 600 may store reference gait data for the wearable robot 1. The reference gait data may include a reference trajectory. The reference trajectory may mean a target trajectory which the individual joints of the wearable robot 1 should follow when the wearer walks. A method of generating the reference trajectory will be briefly described below.

First, a wearer wearing the wearable robot 1 walks with an average stride length and at an average velocity for a desired (or, alternatively, a predetermined) time period. Then, the position sensors and velocity sensors disposed in the individual joints of the wearable robot 1 may sense positions and velocities of the joints while the wearer walks, and the pressure sensors 1000 installed in the foot rest units 42R and 42L may determine whether the foot rest units 42R and 42L have contacted the ground. Gait data sensed by the position sensors, the velocity sensors, and the pressure sensors may be stored in the storage unit 600 and/or an external device (not shown). Thereafter, the stored gait data may be analyzed to detect gait cycles, and an average value of data of the detected gait cycles may be calculated. The average value may be used as the reference trajectory. Therefore, in some example embodiments, the reference trajectory may be generated in advance, and stored in the storage unit 600.

The storage unit 600 which stores the reference trajectory may be a non-volatile memory, a volatile memory, a hard disk, an optical disk, and a combination of two or more of the above-mentioned devices. The storage unit may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM). However, the storage unit 600 is not limited to the above-mentioned devices, and may be another storage device well-known to one of ordinary skill in the art.

The controller 100 may include a processor and a memory (not shown).

The processor may be an arithmetic logic unit, a digital signal processor, a microcomputer, a field programmable array, a programmable logic unit, a microprocessor or any other device capable of responding to and executing instructions in a defined manner such that the processor is programmed with instructions that configure the processor as a special purpose computer to perform the operations illustrated in FIG. 8, such that the controller 100 is configured to estimate the wearer's current gait phase based on the results of sensing by the sensor unit 500. The gait phase may be a phase of a movement cycle of limbs of wearer of the wearable robot 1 during locomotion over the ground. For example, a phase within the gait cycle of FIG. 4. Then, the controller 100 may detect a gait phase among the reference gait data that is similar to the estimated gait phase, for example, a gait phase having a minimum difference from the estimated gait phase, and generate control signals for adjusting driving velocities of the individual drivers 210R, 210L, 310R, 310L, 410R, and 410L such that the estimated gait phase gradually converges into the detected gait phase. The controller 100 will be described in more detail with reference to FIG. 6, below.

The instructions may be stored on a non-transitory computer readable medium, for example, the storage unit 600.

Figure 6:
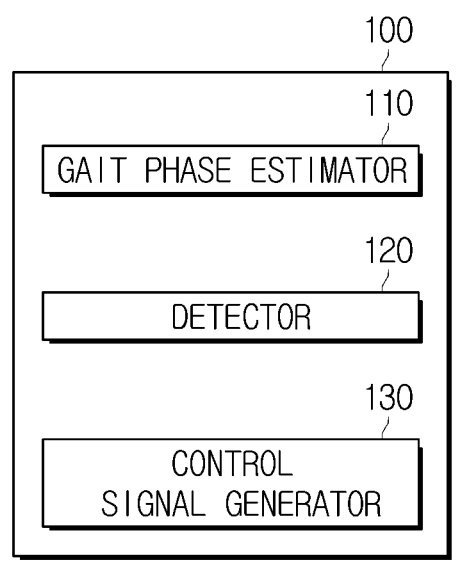
FIG. 6 is a block diagram illustrating a configuration of a controller of FIG. 5.

FIG. 6 is a block diagram illustrating a configuration of the controller 100.

Referring to FIG. 6, the controller 100 may include a gait phase estimator 110, a detector 120, and a control signal generator 130. For example, the controller 100 may be configured to execute instructions that program the controller 100 to perform the functions of one or more of the gait phase estimator 110, the detector 120, and the control signal generator 130.

The gait phase detector 110 may estimate a current gait phase of the wearer based on the results of sensing by the sensor unit 500. For example, the gait phase detector 110 may estimate the current gait phase, based on the results of sensing by the position sensors and the velocity sensors disposed in the individual joints of the wearable robot 1, and the results of sensing by the pressure sensors disposed in the foot rest units 42R and 42L of the wearable robot 1. As such, by estimating the current gait phase, using the position sensors the velocity sensors disposed in the individual joints, and the pressure sensors disposed in the foot rest units 42R and 42L, the current gait phase may be more accurately estimated than when the current gait phase is estimated using only the results of sensing by the position sensors and the velocity sensors.

The gait phase estimator 110 may provide the estimated current gait phase to the detector 120 and the control signal generator 130.

The detector 120 may detect a gait phase among the reference gait data that has a minimum difference from the estimated gait phase.

Figure 7:
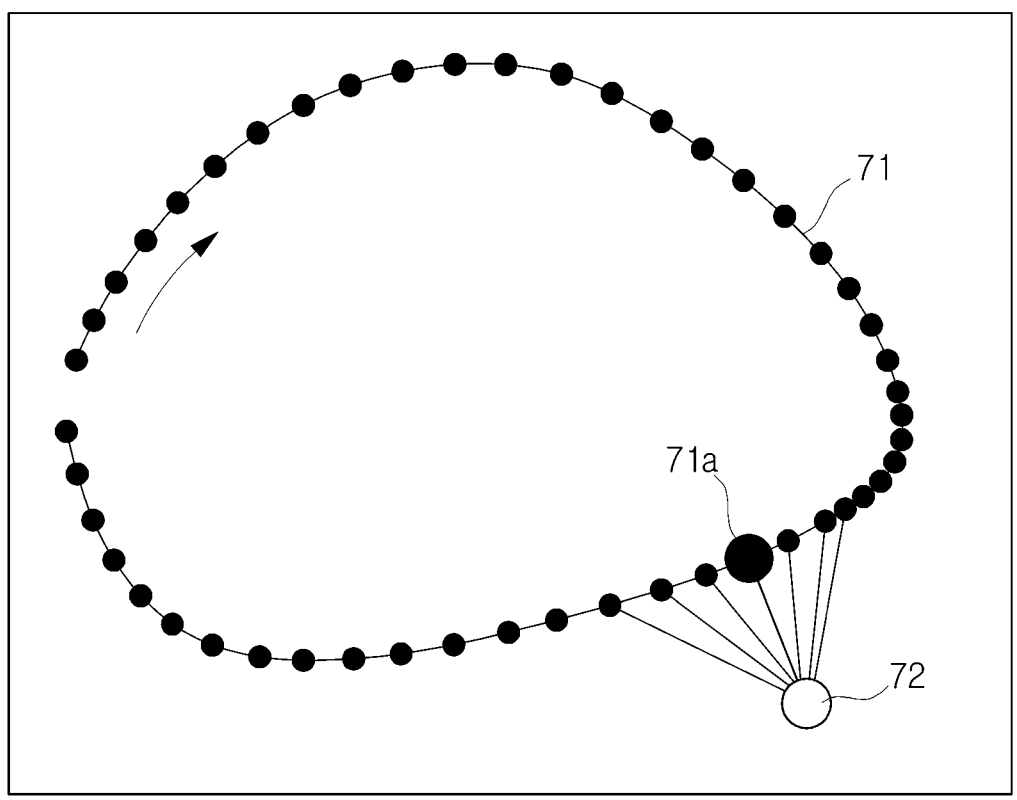
FIG. 7 shows an example of reference gait data.

FIG. 7 shows an example of reference gait data.

Referring to FIG. 7, reference gait data 71 and estimated gait phase 72 may be represented in a 2Dimensional (2D) state space. In this case, the detector 120 may detect a gait phase 71a among the reference gait data 71 that is relatively close to the estimated gait phase 72. In some example, embodiments the detected gait phase 71a may have a minimum difference from the estimated gait phase 72.

As described above, a gait phase estimated based on the results of sensing by the position sensors, the velocity sensors, and the pressure sensors has higher accuracy than a gait phase estimated based on the results of sensing by the position sensors and the velocity sensors. Accordingly, by detecting a gait phase having a minimum difference from an estimated gait phase from reference gait data, accuracy of the detection result may be also improved. The detector 120 may provide the detected gait phase to the control signal generator 130.

The control signal generator 130 may generate control signals for adjusting driving velocities of the individual drivers 210R, 210L, 310R, 310L, 410R, and 410L such that the estimated gait phase gradually converges into the detected gait phase. The control signals generated by the control signal generator 130 are provided to the individual drivers 210R, 210L, 310R, 310L, 410R, and 410L. By controlling the individual drivers 210R, 210L, 310R, 310L, 410R, and 410L in this way, a motion of the wearable robot 1 can be synchronized with the wearer's motion when the wearable robot 1 is controlled according to reference gait data, thereby reducing collisions between the motion of the wearable robot 1 and the wearer's motion.

FIG. 8 is a flowchart illustrating a control method of the wearable robot 1 according to some example embodiments.

Referring to FIG. 8, in operation S81, the controller 100 may generate reference gait data. The reference gait data may include a reference trajectory. The reference trajectory may be a target trajectory which the individual joints of the wearable robot 1 should follow when the wearer walks.

For example, the controller 100 may generate the reference data by having a wearer wearing the wearable robot 1 walk with an average stride length and at an average velocity for a desired (or, alternatively, a predetermined) time period; record, as gait data, positions and velocities of the individual joints of the wearable robot 1, and information about whether the foot rest units 42R and 42L have contacted the ground, while the wearer walks; analyze the recorded gait data to detect gait cycles; and set an average of data of the detected gait cycles to a reference trajectory.

Thereafter, in operation S82, when the wearer wearing the wearable robot 1 walks, various kinds of sensors of the sensor unit 500 may measure and determine positions and velocities of the individual joints, and whether the foot rest units 42R and 42L have contacted the ground.

In operation S83, the gain phase estimator 110 may estimate the gait phase of the wearer based on the results of sensing by the sensor unit 500. For example, the gait phase may be estimated, based on the results of sensing by position sensors and velocity sensors included in the individual joints, and the results of sensing by pressure sensors included in the foot rest units 42R and 42L. As such, by estimating the gait phase using the position sensors, velocity sensors, and pressure sensors, the wearer's gait phase may be more accurately estimated than when the gait phase is estimated using only the position sensors and velocity sensors.

In operation S84, the detector 120 may detect a gait phase among the reference data having a minimum difference from the estimated gait phase, for example, from a reference trajectory.

In operation S85, the control signal generator 130 may generate control signals based on the estimated gait phase and the detected gait phase, and provide the generated control signals to the respective drivers 210R, 210L, 310R, 310L, 410R, and 410L. For example, the control signal generator 130 may generate control signals for adjusting driving velocities of the individual drivers 210R, 210L, 310R, 310L, 410R, and 410L such that the estimated gait phase gradually converges into the detected gait phase.

In operation S86, the drivers 210R, 210L, 310R, 310L, 410R, and 410L may be driven according to the control signals. By controlling the individual drivers 210R, 210L, 310R, 310L, 410R, and 410L in this way, a motion of the wearable robot 1 may be synchronized with the wearer's motion when the wearable robot 1 is controlled according to reference gait data, thereby reducing collisions between the motion of the wearable robot 1 and the wearer's motion.

As described above, according to some example embodiments, since a motion of the wearable robot may be synchronized with a wearer's motion when the wearable robot is controlled based on reference gait data, it is possible to minimize collision between the wearer and the wearable robot.

Since a synchronization time is detected based on the results of sensing by pressure sensors installed in the foot rest units, it is possible to quickly and accurately detect a synchronization time.

Some example embodiments have been described above. In the example embodiments described above, some of components constituting the wearable robot 1 may be implemented as a "module". Here, the term 'module' means, but is not limited to, a software and/or hardware component, such as a Field Programmable Gate Array (FPGA) or Application Specific Integrated Circuit (ASIC), which performs certain tasks. A module may advantageously be configured to reside on the addressable storage medium and configured to execute on one or more processors.

Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The operations provided for in the components and modules may be combined into fewer components and modules or further separated into additional components and modules. In addition, the components and modules may be implemented such that they execute one or more CPUs in a device.

With that being said, and in addition to the above described example embodiments, example embodiments may thus be implemented through computer readable code/instructions in/on a medium, e.g., a computer readable medium, to control at least one processing element to implement any above described embodiment. The medium can correspond to any medium/media permitting the storing and/or transmission of the computer readable code.

The computer-readable code can be recorded on a medium or transmitted through the Internet. The medium may include Read Only Memory (ROM), Random Access Memory (RAM), Compact Disk-Read Only Memories (CD-ROMs), magnetic tapes, floppy disks, and optical recording medium. Also, the medium may be a non-transitory computer-readable medium. The media may also be a distributed network, so that the computer readable code is stored or transferred and executed in a distributed fashion. Still further, as only an example, the processing element could include at least one processor or at least one computer processor, and processing elements may be distributed and/or included in a single device.

Although a few example embodiments have been shown and described, it would be appreciated by those skilled in the art that changes may be made in these example embodiments without departing from the principles and spirit of the disclosure, the scope of which is defined in the claims and their equivalents.

What is claimed is:

1. A control method of a wearable robot, the wearable robot including a plurality of joints, the control method comprising:
    generating a reference trajectory in a two-dimensional state space, the reference trajectory being a trajectory which the plurality of joints are required to follow when the wearable robot assists a wearer with walking;
    sensing motion of the wearer by sensing at least whether one or more of a toe and a heel portion of one or more foot rests associated with the wearable robot is in contact with a ground using a pair of pressure sensors;
    estimating a gait phase of the wearer of the wearable robot in the two-dimensional state space based on at least results of the sensing by the pair of pressure sensors;
    determining a distance between each of the multiple data points in the reference trajectory and the estimated gait phase in the two-dimensional state space;
    detecting a gait phase as one of the multiple data points within the reference trajectory such that the detected gait phase has a minimum distance from the estimated gait phase in the two-dimensional state space; and
    synchronizing motion of the wearable robot with the results of sensing motion of the wearer by the pair of pressure sensors by,
        generating a control signal associated with a driving velocity of a driver of the wearable robot based on the detected gait phase within the reference trajectory such that the estimated gait phase gradually converges to the detected gait phase, and
        driving the driver according to the control signal.

2. The control method according to claim 1, wherein the sensing further comprises:
    sensing, via a position sensor, a position of each of the plurality of joints, and
    sensing, via a velocity sensor, a velocity of each of the plurality of joints.

3. A control method of a wearable robot, the wearable robot including a plurality of joints, the control method comprising:
    sensing motion of a wearer by sensing at least whether one or more of a toe and a heel portion of one or more foot rests associated with the wearable robot is in contact with a ground using a pair of pressure sensors;
    estimating a gait phase of Ran the wearer of the wearable robot in a two-dimensional state space based on at least results of the sensing by the pair of pressure sensors;
    determining a distance between each of multiple data points in a reference trajectory and the estimated gait phase in the two-dimensional state space, the reference trajectory being a trajectory which the plurality of joints are required to follow when the wearable robot assists the wearer with walking;
    detecting a gait phase as one of the multiple data points within the reference trajectory such that the detected gait phase has a minimum distance from the estimated gait phase in the two-dimensional state space; and
    synchronizing motion of the wearable robot with the results of sensing motion of the wearer by the pair of pressure sensors by,
        generating a control signal associated with a driving velocity of a driver of the wearable robot based on the detected gait phase within the reference trajectory such that the estimated gait phase gradually converges to the detected gait phase, and
        driving the driver according to the control signal.

4. The control method according to claim 3, wherein the sensing further comprises:
    sensing, via a position sensor, a position of each of the plurality of joints, and
    sensing, via a velocity sensor, a velocity of each of the plurality of joints.

5. The control method according to claim 3, wherein the wearable robot is pre-programmed with the reference trajectory.

6. A wearable robot comprising:
    a memory configured to store reference trajectory therein;
    a walking assistance device having an exoskeleton shape such that the walking assistance device is configured to be worn on one or more legs of a wearer of the wearable robot, the walking assistance device including a plurality of joints and a plurality of sensors; and
    a controller configured to,
        sense motion of the wearer by sensing at least whether one or more of a toe and a heel portion of one or more foot rests associated with the wearable robot is in contact with a ground using a pair of pressure sensors included in the plurality of sensors,
        estimate a gait phase of the wearer in a two-dimensional state space based on at least results of sensing by the pair of pressure sensors,
        determine a distance between each of multiple data points in the reference trajectory and the estimated gait phase in the two-dimensional state space, the reference trajectory being a trajectory which the plurality of joints are required to follow when the walking assistance device assists the wearer with walking,
        detect a gait phase as one of the multiple data points within the reference trajectory such that the detected gait phase has a minimum distance from the estimated gait phase in the two-dimensional state space, and
        synchronize motion of the wearable robot with the results of sensing motion of the wearer by the pair of pressure sensors by,
            generating a control signal to adjust a driving velocity of a driver based on the detected gait phase within the reference trajectory such that the estimated gait phase gradually converges to the detected gait phase, and
            driving the driver according to the control signal.

7. The wearable robot according to claim 6, wherein the plurality of sensors comprise:
    a position sensor configured to sense a position of each of the plurality of joints,
    a velocity sensor configured to sense a velocity of each of the plurality of joints, and
    the pair of pressure sensors configured to determine whether one or more foot rests associated with the walking assistance device is in contact with the ground.

* * * * *